United States Patent [19]

Doll et al.

[11] 4,294,839

[45] Oct. 13, 1981

[54] BENZOTHIAZOLE DERIVATIVES AND PHARMACEUTICAL FORMULATIONS CONTAINING THEM

[75] Inventors: Thomas Doll, Mainz; Erich Schacht, Seeheim-Jugenheim; Hans-Eckart Radunz, Mühltal; Ernst Schulze, Darmstadt, all of Fed. Rep. of Germany

[73] Assignee: Merck Patent Gesellschaft mit beschrankter Haftung, Darmstadt, Fed. Rep. of Germany

[21] Appl. No.: 215,987

[22] Filed: Dec. 12, 1980

[30] Foreign Application Priority Data

Dec. 13, 1979 [DE] Fed. Rep. of Germany ....... 2950095

[51] Int. Cl.³ .................. A61K 31/425; A61K 31/44; C07D 277/74; C07D 417/12
[52] U.S. Cl. .................................... 424/263; 424/270; 546/270; 548/170; 548/171
[58] Field of Search ................ 546/270; 548/170, 171; 424/263, 270

[56] References Cited

U.S. PATENT DOCUMENTS 2,647,877 8/1953 Dazzi .................................. 548/170

FOREIGN PATENT DOCUMENTS 38-8749 6/1963 Japan .
54-65305 7/1979 Japan .

*Primary Examiner*—Richard Raymond
*Attorney, Agent, or Firm*—Millen & White

[57] ABSTRACT

Benzothiazole derivatives of the formula I

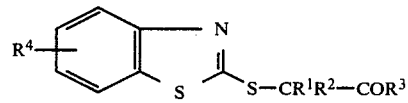

wherein $R^1$ is H or $CH_3$; $R^2$ is phenyl, tolyl, xylyl or pyridyl; $R^3$ is OH, alkoxy of 1–4 C atoms or $-NHCH_2CH_2OH$; and $R^4$ is H, Cl, Br, OH or alkoxy of 1–4 C atoms, and physiologically acceptable salts thereof, have valuable pharmacological properties.

8 Claims, No Drawings

BENZOTHIAZOLE DERIVATIVES AND PHARMACEUTICAL FORMULATIONS CONTAINING THEM

SUMMARY OF THE INVENTION

An object of this invention is to provide new compounds having valuable properties, especially compounds which can be used for the preparation of medicaments.

Upon further study of the specification and appended claims, further objects and advantages of this invention will become apparent to those skilled in the art.

These objects have been attained by this invention by providing new benzothiazole derivatives of formula I

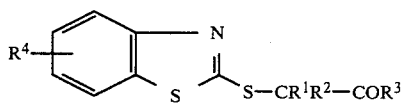

wherein $R^1$ is H or $CH_3$; $R^2$ is phenyl, tolyl, xylyl or pyridyl; $R^3$ is OH, alkoxy of 1–4 C atoms or $-NHCH_2CH_2OH$; and $R^4$ is H, Cl, Br, OH or alkoxy of 1–4 C atoms; and physiologically acceptable salts thereof.

DETAILED DISCUSSION

For $R^2$, tolyl is preferably p-tolyl, but is also o-tolyl or m-tolyl. Xylyl is preferably 2,3-dimethylphenyl, but can also be 2,4- 2,5-, 2,6-, 3,4- or 3,5-dimethylphenyl. Pyridyl is preferably 2-pyridyl, but is also 3-pyridyl or 4-pyridyl. In $R^3$ and $R^4$, alkoxy is preferably methoxy or ethoxy, but is also n-propoxy, isopropoxy, n-butoxy, isobutoxy, sec-butoxy or tert-butoxy.

In particular, $R^1$ is preferably $CH_3$. $R^2$ is preferably phenyl and secondarily p-tolyl, 2,3-dimethylphenyl or 2-pyridyl. $R^3$ is preferably OH, methoxy, ethoxy or $-NHCH_2CH_2OH$. $R^4$ is preferably H, Cl or ethoxy. $R^4$ can, moreover, be in the 4-, 5-, 6- or 7-position in the benzothiazole ring; preferably it is in the 5-position or the 6-position. A radical $R^4=Cl$ is preferably in the 5-position, while a radical $R^4=$alkoxy is preferably in the 6-position.

Accordingly, the present invention relates in particular to those compounds of this invention in which at least one of the defined radicals has one of the meanings indicated above, particularly one of the preferred meanings indicated above. Some preferred groups of compounds can be expressed by means of the following partial formulae Ia to Id, which correspond to formula I, but wherein:

is Ia:
 $R^1$ is H or $CH_3$,
 $R^2$ is phenyl or 2-pyridyl,
 $R^3$ is OH, methoxy, ethoxy or $-NHCH_2CH_2OH$ and
 $R^4$ is H, Cl or ethoxy;
in Ib:
 $R^1$ is H or $CH_3$,
 $R^2$ is phenyl,
 $R^3$ is OH, methoxy or ethoxy and
 $R^4$ is H, Cl or ethoxy;
in Ic:
 $R^1$ is H or $CH_3$,
 $R^2$ is phenyl,
 $R^3$ is OH or ethoxy and
 $R^4$ is H, 5-Cl or 6-ethoxy; and
in Id:
 $R^1$ is H or $CH_3$,
 $R^2$ is phenyl or 2-pyridyl,
 $R^3$ is $-NHCH_2CH_2OH$ and
 $R^4$ is H, Cl or ethoxy.

The compounds of formula I have an asymmetric carbon atom in the side chain. They can have additional asymmetric carbon atoms in the radicals $R^3$ and/or $R^4$. They can, therefore, exist as racemates and, if several asymmetric carbon atoms are present, also in the form of mixtures of several racemates, as well as in various optically active forms.

The present invention further relates to a process for preparing the compounds of formula I and their physiologically acceptable salts, comprising reacting a compound of formula II

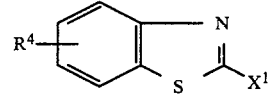

with a compound of formula III $$X^2\text{-}CR^1R^2\text{-}COR^3 \qquad III$$

wherein one of $X^1$ and $X^2$ is SH or SH which has been functionally modified so as to be reactive, the other of these two radicals being Cl, Br, I, OH or OH which has been functionally modified so as to be reactive; and $R^1$ to $R^4$ have the meanings indicated for formula I; and, optionally, saponifying a resulting ester; and/or
esterifying a resulting acid; and/or
amidizing a resulting acid or a resulting ester; and/or
etherifying a resulting phenolic compound; and/or
converting a resulting base or acid, by treatment with an acid or base, respectively, into one of its physiologically acceptable acid addition salts or metal or ammonium salts, respectively.

The preparation of the compounds of formula I is effected in other respects in accordance with methods which are in themselves known, e.g., which are described in the literature (for example in the standard works such as Houben-Weyl, Methoden der organischen Chemie ("Methods of Organic Chemistry"), Georg Thieme-Verlag, Stuttgart; and Organic Reactions, John Wiley & Sons, Inc., New York), in particular under reaction conditions, e.g., which are known and suitable for the described reactions. In these reactions it is also possible to make use of variants which are in themselves known but are not mentioned here in greater detail.

The starting materials of the formulae II and III can, if desired, also be formed in situ, in such a way that they are not isolated from the reaction mixture, but are immediately reacted further to form the compounds of formula I.

In the radicals $X^1$ and/or $X^2$, the SH group can be functionally modified, preferably in the form of a mercaptide, especially a metal mercaptide, for example an alkali metal, alkaline earth metal or heavy metal mercaptide, and preferably in the form of the sodium, potassium, silver, lead, zinc or mercury mercaptide. In the radicals $X^1$ and/or $X^2$, the OH group can be functionally modified, preferably in the form of a reactive ester, for example an alkylsulfonate (wherein the alkyl group has, in particular, 1–6 C atoms, for example methanesulfonyloxy) or an arylsulfonate (wherein the aryl group has, in particular, 6–10 C atoms, for example benzenesulfonyloxy, p-toluenesulfonyloxy, 1-naphthalenesulfonyloxy or 2-naphthalenesulfonyloxy).

Some of the starting materials of the formulae II and III are known; some are new. Those starting materials which are not known can, however, be prepared in analogy with the known starting materials using the methods which are in themselves known. Thus, for example, the 2-halogenobenzothiazoles of the formula II ($X^1$=Cl, Br or I) are obtainable by halogenating the corresponding benzothiazoles (corresponding to formula I, but with H instead of $X^1$) or the corresponding phenyl mustard oils, using, for example, $PCl_5$ or $PBr_5$. The 2-halogenoacetic acid or 2-halogenopropionic acid derivatives of formula III ($X^2$=Cl, Br or I) are similarly accessible by halogenating the acetic acid or propionic acid derivatives, respectively, (corresponding to II, but with H instead of $X^2$) on which they are based. The corresponding mercapto compounds of the formulae II ($X^1$=SH) or III ($X^2$=SH) can be prepared from the halogen compounds by reaction with NaSH.

As a rule, the reaction of II and III is carried out with the addition of a base, for example a metal oxide, such as silver oxide, lead oxide, zinc oxide, mercury oxide or calcium oxide; a metal hydroxide, in particular an alkali metal hydroxide or alkaline earth metal hydroxide, such as NaOH, KOH, LiOH or $Ca(OH)_2$; an alkali metal carbonate or alkaline earth metal carbonate, for example $Na_2CO_3$ or $K_2CO_3$; an alkali metal alcoholate or alkaline earth metal alcoholate, for example sodium methylate or ethylate, or potassium methylate, ethylate or tert-butylate; or an organic base, for example triethylamine or benzyltrimethylammonium hydroxide. In principle, all salt-forming (mercaptide-forming) bases are suitable. The intermediate/product formed in the reaction of the mercapto compound II ($X^1$=SH) or III ($X^2$=SH) with the base is, generally, the corresponding mercaptide. If the reactant used is a halogenocarboxylic acid of the formula III ($R^3$=OH), the latter is also preferably employed in the reaction in the form of one of its salts (for example the Na, K, Li or Ba salt).

The reaction of II with III can be carried out in the absence, or preferably in the presence, of an inert solvent or suspending agent. Examples of suitable solvents or suspending agents include hydrocarbons, such as benzene, toluene or xylene; alcohols, such as methanol, ethanol, isopropanol, n-propanol, n-butanol or tert-butanol; ethers, such as diethyl ether, diisopropyl ether, tetrahydrofuran (THF), dioxane or diethylene glycol dimethyl ether; amides, such as acetamide or dimethylformamide (DMF); nitriles, such as acetonitrile; sulfoxides, such as dimethyl sulfoxide; water; and also mixtures of the solvents mentioned. The reaction is preferably carried out at temperatures of 0° to about 200° C., preferably 20°–150° C.; the reaction time is from about 10 minutes to several days, depending on the conditions used. If the reaction is carried out in the absence of solvent, e.g., by fusing a sodium mercaptide II ($X^1$=SNa) with a bromocarboxylic acid salt (for example of the formula Br-$CR^1R^2$-COONa), higher temperatures are also suitable, up to about 300° C. It can be advantageous to carry out the reaction under an inert gas such as nitrogen or argon.

If desired, the radical $R^3$ in a resulting compound of the formula I can be converted into another radical $R^3$ by treatment with saponifying, ester-forming or amidizing agents.

Thus, a resulting ester of the formula I ($R^3$=alkoxy of 1–4 C atoms) can be saponified by methods which are in themselves known to give the corresponding acid (I, $R^3$=OH), preferably by hydrolysis in an alkaline medium, for example by means of NaOH or KOH in an alcohol, such as methanol, ethanol or isopropanol, if desired with the addition of water, at temperatures of about 0° to about 100° C., preferably of 20° to 80° C.

Resulting acids of the formula I ($R^3$=OH) can be esterified by methods described in the literature, for example by reacting them with the appropriate alcohols of the formula $R^3$-H($R^3$=alkoxy of 1–4 C atoms), preferably in the presence of an inorganic or organic acid, such as HCl, HBr, HI, $H_2SO_4$, $H_3PO_4$, trifluoroacetic acid, benzenesulfonic acid or p-toluenesulfonic acid, or an acid ion exchanger, in the presence or absence of an inert solvent, such as, for example, benzene, toluene or xylene, at temperatures of about 0° to about 150° C. It is preferable to employ an excess of the alcohol. Furthermore, it is possible to carry out the reaction in the presence of water-binding agents, for example anhydrous heavy metal salts (such as $CuSO_4$ or $ZnCl_2$) or molecular sieves. It is also possible to remove the water of reaction azeotropically, in which connection it is advantageous to add hydrocarbons (for example benzene or toluene) or chlorinated hydrocarbons (for example chloroform or 1,2-dichloroethane). The esterification proceeds under gentle conditions if the water of reaction is chemically bound by adding carbodiimides (for example N,N'-dicyclo-hexylcarbodiimide), preferably in equimolar amounts, in which case inert solvents, such as ether, dioxane, benzene or 1,2-dimethoxyethane, can be used and bases, such as pyridine, can be added. The methyl esters (or ethyl esters) can also be prepared by reacting the free acids with diazomethane (or diazoethane respectively) in an inert solvent, such as ether, benzene or methanol.

Furthermore, it is possible to prepare esters by reacting metal salts, preferably the alkali metal, lead or silver salts, of the appropriate acids with alkyl halides corresponding to the appropriate alcohol, if appropriate in an inert solvent, for example ether, benzene or petroleum ether.

It is furthermore possible to convert resulting acids or esters of formula I ($R^3$=OH or alkoxy of 1–4 C atoms), into the corresponding ethanol-amides (formula I, $R^3$=NHCH$_2$CH$_2$OH), by treatment with amidizing agents. A suitable amidizing agent is primarily ethanolamine itself. The reaction is carried out in the presence or absence of an additional inert solvent. Examples of suitable solvents include hydrocarbons, such as benzene, toluene or xylene, halogenated hydrocarbons, such as methylene chloride, chloroform or 1,2-dichloroethane, ethers, such as diethyl ether, THF or dioxane, amides, such as DMF, dimethylacetamide or phosphoric acid hexamethyltriamide. It is also possible to use an excess of ethanolamine as the solvent. The presence of a catalyst or a dehydrating agent can be advisable. The temperatures in the amidation reaction are preferably about −20° to 200° C. If the free acids I ($R^3$=OH) are used as the starting material, it is advantageous to carry out the amidation in two stages by first converting the acid into an acid halide, for example into the chloride by means of thionyl chloride, and then reacting this halide with ethanolamine.

Racemates of formula I can be resolved into their optical antipodes by methods such as are described in the literature. Carboxylic acids of formula I ($R^3$=OH) can be converted, for example by means of optically active amines, such as quinine, brucine or strychnine, into diastereomeric salts, which are separated by crystallization and can be split up by hydrolysis.

A basic compound of formula I can be converted into the appropriate acid addition salt by means of an acid. Acids which give physiologically acceptable salts are suitable for this reaction. Thus, it is possible to use inorganic acids, for example sulfuric acid, nitric acid, hydrogen halide acids, such as hydrochloric acid or hydrobromic acid, or phosphoric acids, such as orthophosphoric acid, and also organic acids, in particular aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicyclic acid, 2-phenylpropionic acid, 3-phenyl-propionic acid, citric acid, gluconic acid, ascorbic acid, nicotinic acid, isonicotinic acid, methanesulfonic acid, ethanesulfonic acid, ethanedisulfonic acid, 2-hydroxy-ethanesulfonic acid, benzenesulfonic acid, p-toluene-sulfonic acid, naphthalenemonosulfonic acid, naphthalene-disulfonic acid or laurylsulfuric acid.

On the other hand, it is possible to convert acid compounds of formula I into one of their physiologically acceptable metal salts or ammonium salts by reaction with a base. Suitable salts include, in particular, the sodium, potassium, magnesium, calcium and ammonium salts, and also substituted ammonium salts, for example the dimethylammonium, diethylammonium, diisopropylammonium, monoethanolammonium, diethanolammonium, triethanolammonium, cyclohexylammonium, dicyclohexylammonium and dibenzylethylenediammonium salts.

Conversely, compounds of formula I can be liberated from their acid addition salts by treatment with strong bases, or from their metal salts and ammonium salts by treatment with acids.

It has been found that the compounds of this invention and their physiologically acceptable salts possess valuable pharmacological properties and are well tolerated. In particular, they exhibit an antiarteriosclerotic action and a reducing action on the lipid level. Thus, they have both a reducing action on the cholesterol level and a reducing action on the triglyceride level.

The determination of serum cholesterol and of serum triglycerides can be carried out by a fully automatic, enzymatic method devised by Christ, G. A. et al. (Technicon Symposium 1978, Frankfurt) modelled on the procedure for the determination of cholesterol indicated by Röschlau (Röschau, P. et al. (1975), 9th Int. Congr. on Clin. Chemistry, Toronto, Abstr. No. 1) and the determination of triglycerides published by Wieland (H. U. Bergmeyer (Ed.), Methoden der enzymatischen Analyse, Chemie ("Methods of Enzymatic Analysis, Chemie, Weinheim Bergstrasse," 1962).

Furthermore, the ratio of α-lipoproteins and β-lipoproteins is shifted in the direction of increasing α-lipoprotein. The determination of the lipoproteins can be effected with the aid of a polyanionic procedure indicated by Kostner (Kostner, G. M. (1976), Clin. Chemistry 22, 5, 695) and subsequent determination of the HDL-cholesterol as indicated above.

The compounds of the formula I can, therefore, be used as active compounds for medicaments in human and veterinary medicine. They can also be used as intermediate products for the preparation of other active compounds for medicaments.

The invention also relates to the use of the compounds of formula I for the preparation of pharmaceutical formulations, in particular by a non-chemical route. In this connection, the compounds (or one of their physiologically acceptable salts) can be brought into a suitable dosage form together with at least one solid, liquid or semi-liquid excipient or adjuvant and, if appropriate, in combination with one or more additional active compound(s).

The present invention further relates to agents, in particular pharmaceutical formulations, characterized in that they contain at least one compound of formula I and/or one of its physiologically acceptable salts.

These formulations can be used as medicaments in human or veterinary medicine. Possible excipients are organic or inorganic substances which are suitable for enteral (for example oral) or parenteral administration or topical application and which do not react with the new compounds, for example, water, vegetable oils, benzyl alcohols, polyethylene glycols, glycerol triacetate, gelatine, carbohydrates, such as lactose or starch, magnesium stearate, talc or petroleum jelly. Tablets, dragees, capsules, syrups, elixirs or drops are used especially for oral administration, suppositories are used for rectal administration, solutions, preferably oily or aqueous solutions, and also suspensions, emulsions or implants are used for parenteral administration and ointments, creams or powders are used for topical application. If the medicaments are to be administered in the form of doses of powders, the packaging materials, such as paper slips or paper capsules, are also suitable excipients. The new compounds can also be lyophilized and the resulting lyophilizates can be used, for example, for preparing injection formulations. The formulations indicated can be sterilized and/or can contain adjuvants, such as lubricants, preservatives, stabilizing agents and/or wetting agents, emulsifiers, salts for regulating the osmotic pressure, buffer substances, colorants, flavoring substances and/or aroma generating substances. They can, if desired, also contain one or more additional active compounds, for example one or more vitamins.

The invention further relates to the use of the compounds of formula I in the therapeutic treatment of the human body and also in combating diseases. In particular, the compounds of formula I are suitable for the treatment and/or prophylaxis of clinical situations involving increased values of serum lipds and/or shifts of lipoprotein in the direction of the LDL and/or VLDL fractions, of primary and secondary hyperlipoproteinaemias with and without xanthomatosis, of atherosclerosis (coronary arteriosclerosis, cerebral sclerosis or peripheral vascular sclerosis) and of diabetic angiopathies (diabetic retinopathy).

In this connection the substances of this invention are generally administered in analogy with known, commercially available agents which lower the lipid level (for example clofibrate), preferably in dosages of about 10 to 1,000 mg, in particular of 50–500 mg, per dosage unit. The daily dosage is preferably about 0.2 to 100 mg/kg of body weight. The particular dose for each specific patient depends, however, on a very diverse range of factors, for example on the activity of the particular compound employed, on the age, body weight, general state of health, diet and the sex of the host, on the point in time and method of administration, on the rate of elimination and on the combination of medicaments and the severity of the particular disease to which the therapy is applied. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degress Celsius; unless otherwise indicated all parts and percentages are by weight.

Each of the individual compounds of formula I mentioned in the examples which follow is particularly suitable for the preparation of pharmaceutical formulations.

In the examples which follow, "working up in the customary manner" has the following meaning: water is added, if necessary, the mixture is extracted with ether, the phases are separated, the organic phase is dried over sodium sulphate, filtered and evaporated and the product is purified by chromatography (on silica gel) and/or by crystallization.

EXAMPLE 1

2.3 g of Na is dissolved in 80 ml of ethanol; 21.1 g of 6-ethoxy-2-mercaptobenzothiazole is added and the mixture is stirred until solution takes place. 25.7 g of 2-bromo-2-phenylpropionic acid ethyl ester is then added and the mixture is stirred overnight at 20° and worked up in the customary manner to give 2-(6-ethoxybenzothiazol-2-ylthio)-2-phenylpropionic acid ethyl ester, m.p. 92°–94°.

EXAMPLES 2 TO 45

The following are obtained analogously to Example 1 from the corresponding benzothiazol-2-yl mercaptides and the corresponding 2-chloroacetic, 2-bromoacetic, 2-chloropropionic or 2-bromopropionic acid esters:

2. 2-(Benzothiazol-2-ylthio)-2-phenylacetic acid ethyl ester, oil.
3. 2-(Benzothiazol-2-ylthio)-2-phenylpropionic acid ethyl ester, oil.
4. 2-(Benzothiazol-2-ylthio)-2-p-tolylacetic acid ethyl ester.
5. 2-(Benzothiazol-2-ylthio)-2-p-tolylpropionic acid ethyl ester.
6. 2-(Benzothiazol-2-ylthio)-2-(2,3-dimethylphenyl)-acetic acid ethyl ester.
7. 2-(Benzothiazol-2-ylthio)-2-(2,3-dimethylphenyl)-propionic acid ethyl ester.
8. 2-(Benzothiazol-2-ylthio)-2-(2-pyridyl)-acetic acid ethyl ester, oil.
9. 2-(Benzothiazol-2-ylthio)-2-(2-pyridyl)-propionic acid ethyl ester.
10. 2-(Benzothiazol-2-ylthio)-2-(3-pyridyl)-acetic acid ethyl ester.
11. 2-(Benzothiazol-2-ylthio)-2-(3-pyridyl)-propionic acid ethyl ester.
12. 2-(Benzothiazol-2-ylthio)-2-(4-pyridyl)-acetic acid ethyl ester.
13. 2-(Benzothiazol-2-ylthio)-2-(4-pyridyl)-propionic acid ethyl ester.
14. 2-(4-Chlorobenzothiazol-2-ylthio)-2-phenylacetic acid ethyl ester.
15. 2-(5-Chlorobenzothiazol-2-ylthio)-2-phenylacetic acid ethyl ester, m.p. 62°–64°.
16. 2-(5-Chlorobenzothiazol-2-ylthio)-2-phenylpropionic acid ethyl ester, m.p. 72°–73°.
17. 2-(5-Chlorobenzothiazol-2-ylthio)-2-p-tolylacetic acid ethyl ester.
18. 2-(5-Chlorobenzothiazol-2-ylthio)-1-p-tolylpropionic acid ethyl ester.
19. 2-(5-Chlorobenzothiazol-2-ylthio)-2-(2,3-dimethylphenyl)-acetic acid ethyl ester.
20. 2-(5-Chlorobenzothiazol-2-ylthio)-2-(2,3-dimethylphenyl)-propionic acid ethyl ester.
21. 2-(5-Chlorobenzothiazol-2-ylthio)-2-(2-pyridyl)-acetic acid ethyl ester, m.p. 105°–107°.
22. 2-(5-Chlorobenzothiazol-2-ylthio)-2-(2-pyridyl)-propionic acid ethyl ester.
23. 2-(5-Chlorobenzothiazol-2-ylthio)-2-(3-pyridyl)-acetic acid ethyl ester.
24. 2-(5-Chlorobenzothiazol-2-ylthio)-2-(3-pyridyl)-propionic acid ethyl ester.
25. 2-(5-Chlorobenzothiazol-2-ylthio)-2-(4-pyridyl)-acetic acid ethyl ester.
26. 2-(5-Chlorobenzothiazol-2-ylthio)-2-(4-pyridyl)-propionic acid ethyl ester.
27. 2-(6-Chlorobenzothiazol-2-ylthio)-2-phenylacetic acid ethyl ester.
28. 2-(7-Chlorobenzothiazol-2-ylthio)-2-phenylacetic acid ethyl ester.
29. 2-(5-Bromobenzothiazol-2-ylthio)-2-phenylacetic acid ethyl ester.
30. 2-(5-Bromobenzothiazol-2-ylthio)-2-phenylpropionic acid ethyl ester.
31. 2-(6-Hydroxybenzothiazol-2-ylthio)-2-phenylacetic acid ethyl ester.
32. 2-(6-Hydroxybenzothiazol-2-ylthio)-2-phenylpropionic acid ethyl ester.
33. 2-(6-Methoxybenzothiazol-2-ylthio)-2-phenylacetic acid ethyl ester.
34. 2-(6-Ethoxybenzothiazol-2-ylthio)-2-phenylacetic acid ethyl ester, m.p. 92°–94°.
35. 2-(6-Ethoxybenzothiazol-2-ylthio)-2-p-tolylacetic acid ethyl ester.
36. 2-(6-Ethoxybenzothiazol-2-ylthio)-2-p-tolylpropionic acid ethyl ester.
37. 2-(6-Ethoxybenzothiazol-2-ylthio)-2-(2,3-dimethylphenyl)-acetic acid ethyl ester.
38. 2-(6-Ethoxybenzothiazol-2-ylthio)-2-(2,3-dimethylphenyl)-propionic acid ethyl ester.
39. 2-(6-Ethoxybenzothiazol-2-ylthio)-2-(2-pyridyl)-acetic acid ethyl ester, m.p. 111°–113°.
40. 2-(6-Ethoxybenzothiazol-2-ylthio)-2-(2-pyridyl)-propionic acid ethyl ester.
41. 2-(6-Ethoxybenzothiazol-2-ylthio)-2-(3-pyridyl)-acetic acid ethyl ester. p1 42. 2-(6-Ethoxybenzothiazol-2-ylthio)-2-(3-pyridyl)-propionic acid ethyl ester.
43. 2-(6-Ethoxybenzothiazol-2-ylthio)-2-(4-pyridyl)-acetic acid ethyl ester.
44. 2-(6-Ethoxybenzothiazol-2-ylthio)-2-(4-pyridyl)-propionic acid ethyl ester.
45. 2-(6-n-Butoxybenzothiazol-2-ylthio)-2-phenylacetic acid ethyl ester.

EXAMPLE 46

2.3 g of sodium is dissolved in 250 ml of ethanol; 13.5 g of 2-mercaptobenzothiazole, followed by 17.1 g of 2-chloro-2-phenylacetic acid, is added and the mixture is boiled under reflux for 6 hours. It is then cooled, the sodium salt which has precipitated is filtered off and dissolved in water; and the solution is washed with water, acidified with hydrochloric acid and worked up in the customary manner. This gives 2-(benzothiazol-2-ylthio)-2-phenylacetic acid, m.p. 152°–154°.

EXAMPLE 47

2-(Benzothiazol-2-ylthio)-2-phenylacetic acid 2-hydroxyethylamide, m.p. 135°–138°, is obtained analogously to Example 1 from 2-mercaptobenzothiazole and 2-bromo-2-phenylacetic acid 2-hydroxyethylamide.

EXAMPLE 48

18.2 g of 2-mercapto-2-phenylacetic acid methyl ester is added to a suspension of 2.4 g of NaH in 200 ml of DMF and the mixture is stirred until the evolution of gas has ceased. 17 g of 2-chlorobenzothiazole (or 21.5 g of 2-bromobenzothiazole) is then introduced. The mixture is stirred for 5 hours at 80° and is worked up in the customary manner to give 2-(benzothiazol-2-ylthio)-2-phenylacetic acid methyl ester, in the form of an oil.

EXAMPLE 49

A mixture of 21.4 g of 2-chloro-6-ethoxybenzothiazole, 22.6 g of the disodium salt of 2-mercapto-2-phenylpropionic acid and 200 ml of n-butanol is boiled for 4 hours and is evaporated and worked up in the customary manner to give 2-(6-ethoxybenzothiazol-2-ylthio)-2-phenylpropionic acid, m.p. 152°–153°.

EXAMPLE 50

6 g of 2-(6-ethoxybenzothiazol-2-ylthio)-2-phenylpropionic acid ethyl ester and 6 g of KOH in 100 ml of ethanol are stirred at 20°; the mixture is evaporated; the residue is dissolved in water; and the solution is washed with ether, acidified with hydrochloric acid and extracted with $CH_2Cl_2$. The phases are separated and the organic phase is dried and evaporated to give 2-(6-ethoxybenzothiazol-2-ylthio)-2-phenylpropionic acid. M.p. 152°–153° (from $CCl_4$).

EXAMPLES 51 TO 94

The following are obtained analogously to Example 50 by saponifying the corresponding esters:
51. 2-(Benzothiazol-2-ylthio)-2-phenylacetic acid, m.p. 152°–154°.
52. 2-(Benzothiazol-2-ylthio)-2-phenylpropionic acid, m.p. 124°–126°.
53. 2-(Benzothiazol-2-ylthio)-2-p-tolylacetic acid.
54. 2-(Benzothiazol-2-ylthio)-2-p-tolylpropionic acid.
55. 2-(Benzothiazol-2-ylthio)-2-(2,3-dimethylphenyl)-acetic acid.
56. 2-(Benzothiazol-2-ylthio)-2-(2,3-dimethylphenyl)-propionic acid.
57. 2-(Benzothiazol-2-ylthio)-2-(2-pyridyl)-acetic acid.
58. 2-(Benzothiazol-2-ylthio)-2-(2-pyridyl)-propionic acid.
59. 2-(Benzothiazol-2-ylthio)-2-(3-pyridyl)-acetic acid.
60. 2-(Benzothiazol-2-ylthio)-2-(3-pyridyl)-propionic acid.
61. 2-(Benzothiazol-2-ylthio)-2-(4-pyridyl)-acetic acid.
62. 2-(Benzothiazol-2-ylthio)-2-(4-pyridyl)-propionic acid.
63. 2-(4-Chlorobenzothiazol-2-ylthio)-2-phenylacetic acid.
64. 2-(5-Chlorobenzothiazol-2-ylthio)-2-phenylacetic acid, m.p. 189°–190°.
65. 2-(5-Chlorobenzothiazol-2-ylthio)-2-phenylpropionic acid, m.p. 172°–173°.
66. 2-(5-Chlorobenzothiazol-2-ylthio)-2-p-tolylacetic acid.
67. 2-(5-Chlorobenzothiazol-2-ylthio)-2-p-tolylpropionic acid.
68. 2-(5-Chlorobenzothiazol-2-ylthio)-2-(2,3-dimethylphenyl)-acetic acid.
69. 2-(5-Chlorobenzothiazol-2-ylthio)-2-(2,3-dimethylphenyl)-propionic acid.
70. 2-(5-Chlorobenzothiazol-2-ylthio)-2-(2-pyridyl)-acetic acid.
71. 2-(5-Chlorobenzothiazol-2-ylthio)-2-(2-pyridyl)-propionic acid.
72. 2-(5-Chlorobenzothiazol-2-ylthio)-2-(3-pyridyl)-acetic acid.
73. 2-(5-Chlorobenzothiazol-2-ylthio)-2-(3-pyridyl)-propionic acid.
74. 2-(5-Chlorobenzothiazol-2-ylthio)-2-(4-pyridyl)-acetic acid.
75. 2-(5-Chlorobenzothiazol-2-ylthio)-2-(4-pyridyl)-propionic acid.
76. 2-(6-Chlorobenzothiazol-2-ylthio)-2-phenylacetic acid.
77. 2-(7-Chlorobenzothiazol-2-ylthio)-2-phenylacetic acid.
78. 2-(5-Bromobenzothiazol-2-ylthio)-2-phenylacetic acid.
79. 2-(5-Bromobenzothiazol-2-ylthio)-2-phenylpropionic acid.
80. 2-(6-Hydroxybenzothiazol-2-ylthio)-2-phenylacetic acid.
81. 2-(6-Hydroxybenzothiazol-2-ylthio)-2-phenylpropionic acid.
82. 2-(6-Methoxybenzothiazol-2-ylthio)-2-phenylacetic acid.
83. 2-(6-Ethoxybenzothiazol-2-ylthio)-2-phenylacetic acid, m.p. 128°–130°.
84. 2-(6-Ethoxybenzothiazol-2-ylthio)-2-p-tolylacetic acid.
85. 2-(6-Ethoxybenzothiazol-2-ylthio)-2-p-tolylpropionic acid.
86. 2-(6-Ethoxybenzothiazol-2-ylthio)-2-(2,3-dimethylphenyl)-acetic acid.
87. 2-(6-Ethoxybenzothiazol-2-ylthio)-2-(2,3-dimethylphenyl)-propionic acid.
88. 2-(6-Ethoxybenzothiazol-2-ylthio)-2-(2-pyridyl)-acetic acid.
89. 2-(6-Ethoxybenzothiazol-2-ylthio)-2-(2-pyridyl)-propionic acid.
90. 2-(6-Ethoxybenzothiazol-2-ylthio)-2-(3-pyridyl)-acetic acid.
91. 2-(6-Ethoxybenzothiazol-2-ylthio)-2-(3-pyridyl)-propionic acid.
92. 2-(6-Ethoxybenzothiazol-2-ylthio)-2-(4-pyridyl)-acetic acid.
93. 2-(6-Ethoxybenzothiazol-2-ylthio)-2-(4-pyridyl)-propionic acid.
94. 2-(6-n-Butoxybenzothiazol-2-ylthio)-2-phenylacetic acid.

EXAMPLE 95

A solution of 1 g of 2-(benzothiazol-2-ylthio)-2-phenylacetic acid in 15 ml of ethanolic hydrochloric acid is allowed to stand for 24 hours at 20° and is evaporated and worked up in the customary manner to give 2-(benzothiazol-2-ylthio)-2-phenylacetic acid ethyl ester, in the form of an oil.

EXAMPLES 96 TO 101

The following are obtained from the acid analogously to Example 95 by reaction with the corresponding alcohols:

96. 2-(6-Ethoxybenzothiazol-2-ylthio)-2-phenylpropionic acid methyl ester.
97. 2-(6-Ethoxybenzothiazol-2-ylthio)-2-phenylpropionic acid propyl ester.
98. 2-(6-Ethoxybenzothiazol-2-ylthio)-2-phenylpropionic acid isopropyl ester.
99. 2-(6-Ethoxybenzothiazol-2-ylthio)-2-phenylpropionic acid butyl ester.
100. 2-(6-Ethoxybenzothiazol-2-ylthio)-2-phenylpropionic acid isobutyl ester.
101. 2-(6-Ethoxybenzothiazol-2-ylthio)-2-phenylpropionic acid sec.-butyl ester.

EXAMPLE 102

1 g of 2-(benzothiazol-2-ylthio)-2-phenylacetic acid is dissolved in 20 ml of THF, an ethereal solution of diazomethane is added dropwise until a yellow coloration is produced and the mixture is evaporated to give 2-(benzothiazol-2-ylthio)-2-phenylacetic acid methyl ester, in the form of an oil.

EXAMPLE 103

3.59 g of 2-(6-ethoxybenzothiazol-2-ylthio)-2-phenylpropionic acid is dissolved in 15 ml of phosphoric acid hexamethyltriamide; 0.8 ml of thionyl chloride is added at $-10°$; the mixture is stirred for 2 hours at $-5°$; and 2.5 ml of ethanolamine are added. After stirring overnight at 20°, the mixture is poured onto ice and is worked up in the customary manner. This gives 2-(6-ethoxybenzothiazol-2-ylthio)-2-phenylpropionic acid 2-hydroxyethylamide.

EXAMPLES 104 TO 142

The following are obtained analogously to Example 103 from the corresponding acids:

104. 2-(Benzothiazol-2-ylthio)-2-phenylacetic acid 2-hydroxyethylamide, m.p. 135°–138°.
105. 2-(Benzothiazol-2-ylthio)-2-phenylpropionic acid 2-hydroxyethylamide.
106. 2-(Benzothiazol-2-ylthio)-2-p-tolylacetic acid 2-hydroxyethylamide.
107. 2-(Benzothiazol-2-ylthio)-2-p-tolylpropionic acid 2-hydroxyethylamide.
108. 2-(Benzothiazol-2-ylthio)-2-(2,3-dimethylphenyl)-acetic acid 2-hydroxyethylamide.
109. 2-(Benzothiazol-2-ylthio)-2-(2,3-dimethylphenyl)-propionic acid 2-hydroxyethylamide.
110. 2-(Benzothiazol-2-ylthio)-2-(2-pyridyl)-acetic acid 2-hydroxyethylamide.
111. 2-(Benzothiazol-2-ylthio)-2-(2-pyridyl)-propionic acid 2-hydroxyethylamide.
112. 2-(Benzothiazol-2-ylthio)-2-(3-pyridyl)-acetic acid 2-hydroxyethylamide.
113. 2-(Benzothiazol-2-ylthio)-2-(3-pyridyl)-propionic acid 2-hydroxyethylamide.
114. 2-(Benzothiazol-2-ylthio)-2-(4-pyridyl)-acetic acid 2-hydroxyethylamide.
115. 2-(Benzothiazol-2-ylthio)-2-(4-pyridyl)-propionic acid 2-hydroxyethylamide.
116. 2-(5-Chlorobenzothiazol-2-ylthio)-2-phenylacetic acid 2-hydroxyethylamide, m.p. 142°–144°.
117. 2-(5-Chlorobenzothiazol-2-ylthio)-2-phenylpropionic acid 2-hydroxyethylamide.
118. 2-(5-Chlorobenzothiazol-2-ylthio)-2-p-tolylacetic acid 2-hydroxyethylamide.
119. 2-(5-Chlorobenzothiazol-2-ylthio)-2-p-tolylpropionic acid 2-hydroxyethylamide.
120. 2-(5-Chlorobenzothiazol-2-ylthio)-2-(2,3-dimethylphenyl)-acetic acid 2-hydroxyethylamide.
121. 2-(5-Chlorobenzothiazol-2-ylthio)-2-(2,3-dimethylphenyl)-propionic acid 2-hydroxyethylamide.
122. 2-(5-Chlorobenzothiazol-2-ylthio)-2-(2-pyridyl)-acetic acid 2-hydroxyethylamide.
123. 2-(5-Chlorobenzothiazol-2-ylthio)-2-(2-pyridyl)-propionic acid 2-hydroxyethylamide.
124. 2-(5-Chlorobenzothiazol-2-ylthio)-2-(3-pyridyl)-acetic acid 2-hydroxyethylamide.
125. 2-(5-Chlorobenzothiazol-2-ylthio)-2-(3-pyridyl)-propionic acid 2-hydroxyethylamide.
126. 2-(5-Chlorobenzothiazol-2-ylthio)-2-(4-pyridyl)-acetic acid 2-hydroxyethylamide.
127. 2-(5-Chlorobenzothiazol-2-ylthio)-2-(4-pyridyl)-propionic acid 2-hydroxyethylamide.
128. 2-(5-Bromobenzothiazol-2-ylthio)-2-phenylacetic acid 2-hydroxyethylamide.
129. 2-(5-Bromobenzothiazol-2-ylthio)-2-phenylpropionic acid 2-hydroxyethylamide.
130. 2-(6-Hydroxybenzothiazol-2-ylthio)-2-phenylacetic acid 2-hydroxyethylamide.
131. 2-(6-Hydroxybenzothiazol-2-ylthio)-2-phenylpropionic acid 2-hydroxyethylamide.
132. 2-(6-Ethoxybenzothiazol-2-ylthio)-2-phenylacetic acid 2-hydroxyethylamide, m.p. 135°–137°.
133. 2-(6-Ethoxybenzothiazol-2-ylthio)-2-p-tolylacetic acid 2-hydroxyethylamide.
134. 2-(6-Ethoxybenzothiazol-2-ylthio)-2-p-tolylpropionic acid 2-hydroxyethylamide.
135. 2-(6-Ethoxybenzothiazol-2-ylthio)-2-(2,3-dimethylphenyl)-acetic acid 2-hydroxyethylamide.
136. 2-(6-Ethoxybenzothiazol-2-ylthio)-2-(2,3-dimethylphenyl)-propionic acid 2-hydroxyethylamide.
137. 2-(6-Ethoxybenzothiazol-2-ylthio)-2-(2-pyridyl)-acetic acid 2-hydroxyethylamide.
138. 2-(6-Ethoxybenzothiazol-2-ylthio)-2-(2-pyridyl)-propionic acid 2-hydroxyethylamide.
139. 2-(6-Ethoxybenzothiazol-2-ylthio)-2-(3-pyridyl)-acetic acid 2-hydroxyethylamide.
140. 2-(6-Ethoxybenzothiazol-2-ylthio)-2-(3-pyridyl)-propionic acid 2-hydroxyethylamide.
141. 2-(6-Ethoxybenzothiazol-2-ylthio)-2-(4-pyridyl)-acetic acid 2-hydroxyethylamide.
142. 2-(6-Ethoxybenzothiazol-2-ylthio)-2-(4-pyridyl)-propionic acid 2-hydroxyethylamide.

EXAMPLE 143

3.59 g. of 2-(6-hydroxybenzothiazol-2-ylthio)-2-phenylpropionic acid ethyl ester is dissolved in 15 ml of 1 N sodium hydroxide solution and 1.6 g of diethyl sulfate is added dropwise, while stirring. After stirring for a total of 1 hour, the mixture is worked up in the customary manner to give 2-(6-ethoxybenzothiazol-2-ylthio)-2-phenylpropionic acid ethyl ester, m.p. 92°–94°.

The following examples relate to pharmaceutical formulations containing the compounds of formula I:

EXAMPLE A

Tablets

A mixture of 1 kg of 2-(5-chlorobenzothiazol-2-ylthio)-2-phenylpropionic acid ethyl ester, 4 kg of lactose, 1.2 kg of potato starch, 0.2 kg of talc and 0.1 kg of magnesium stearate is compressed in a customary manner to give tablets, each tablet containing 10 mg of active compound.

EXAMPLE B

Dragees

Tablets are compressed analogously to Example A and are then coated in a customary manner with a coating consisting of sucrose, potato starch, talc, tragacanth and colorant.

EXAMPLE C

Capsules 2 kg of 2-(6-ethoxybenzothiazol-2-ylthio)-2-phenylpropionic acid is filled in a customary manner into hard gelatine capsules, each capsule containing 20 mg of the active compound.

Tablets, dragees and capsules containing one or more of the remaining active compounds of formula I and/or of their physiologically acceptable salts, can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A benzothiazole derivative of the formula

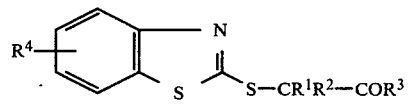

wherein $R^1$ is H or $CH_3$; $R^2$ is phenyl, tolyl, xylyl or pyridyl; $R^3$ is OH, alkoxy of 1-4 C atoms or $-NHCH_2CH_2OH$; and $R^4$ is H, Cl, Br, OH or alkoxy of 1-4 C atoms,
or a physiologically acceptable salt thereof.

2. A compound of claim 1 wherein $R_1$ is $CH_3$.
3. A compound of claim 1 wherein $R_2$ is phenyl, p-tolyl, 2,3-dimethylphenyl or 2-pyridyl.
4. A compound of claim 1 wherein $R_3$ is OH, $-OCH_3$, $-OC_2H_5$ or $-NHCH_2CH_2OH$.
5. A compound of claim 1 wherein $R_4$ is H, Cl or $-OC_2H_5$.
6. 2-(6-ethoxy-benzothiazol-2-yltio)-2-phenylpropionic acid, or
2-(6-ethoxy-benzothiazol-2-ylthio)-2-phenylpropionic acid ethyl ester, compounds of claim 1.
7. A pharmaceutical composition comprising an amount of a compound of claim 1 effective to lower the lipid level in a patient, and a pharmaceuutically acceptable carrier.
8. A method of lowering the lipid level in a patient in need of such lowering, comprising administering to the patient an amount of a compound of claim 1 effective for such lowering.

* * * * *

Disclaimer 4,294,839.—*Thomas Doll*, Mainz; *Erich Schacht*, Seeheim-Jugenheim; *Hans-Eckart Radunz*, Muhltal and *Ernst Schulze*, Darmstadt, Fed. Rep. of Germany. BENZOTHIAZOLE DERIVATIVES AND PHARMACEUTICAL FORMULATIONS CONTAINING THEM. Patent dated Oct. 13, 1981. Disclaimer filed July 6, 1984, by the assignee, *Merck Patent Gesellschaft Mit Beschrankter Haftung.*

Hereby enters this disclaimer to claims 1, 3, 4 and 5 of said patent.
[*Official Gazette June 4, 1985.*]